United States Patent
Castillo et al.

(10) Patent No.: US 12,043,849 B2
(45) Date of Patent: Jul. 23, 2024

(54) PROTEIN PURIFICATION METHOD AND KIT

(71) Applicant: Exothera SA, Charleroi (BE)

(72) Inventors: José Castillo, Brussels (BE); Vasily Medvedev, Nivelles (BE)

(73) Assignee: EXOTHERA SA, Nivelles (BE)

( * ) Notice: Subject to any disclaimer, the term of this patent is extended or adjusted under 35 U.S.C. 154(b) by 1154 days.

(21) Appl. No.: 16/499,355

(22) PCT Filed: Mar. 30, 2018

(86) PCT No.: PCT/EP2018/058365
§ 371 (c)(1),
(2) Date: Sep. 30, 2019

(87) PCT Pub. No.: WO2018/178375
PCT Pub. Date: Oct. 4, 2018

(65) Prior Publication Data
US 2021/0095261 A1   Apr. 1, 2021

(30) Foreign Application Priority Data

Mar. 30, 2017 (BE) .................................. 2017/5211

(51) Int. Cl.
*C12N 7/06* (2006.01)
*C07K 1/18* (2006.01)
*C12Q 1/00* (2006.01)

(52) U.S. Cl.
CPC .................. *C12N 7/06* (2013.01); *C07K 1/18* (2013.01); *C12Q 1/00* (2013.01)

(58) Field of Classification Search
None
See application file for complete search history.

(56) References Cited

FOREIGN PATENT DOCUMENTS

| | | |
|---|---|---|
| EP | 0893450 A1 | 1/1999 |
| WO | 2009058812 A1 | 5/2009 |

OTHER PUBLICATIONS

Valdes R et al: Chromatographic removal combined with heat, acid and chaotropic inactivation of four model viruses, Journal of Biotechnology, Elsevier, Amsterdam, NL, vol. 96, No. 3, Jul. 3, 2002, pp. 251-258.
Glen R. Bolton et al: "Inactivation of viruses using novel protein A wash buffers," Biotechnology Progress, vol. 31, No. 2, Dec. 19, 2014, pp. 406-413.
Vietnamese Examination Report with English translation mailed Jun. 29, 2022 for Vietnamese Application No. 1-2019-05702, 3 pages.

*Primary Examiner* — Benjamin P Blumel
(74) *Attorney, Agent, or Firm* — Dickinson Wright PLLC

(57) ABSTRACT

The invention provides a method and a kit for combined virus inactivation and capture/purification of a feed containing a protein of interest. The method comprises the steps of: contacting a feed comprising a protein of interest with negatively charged particles or media, conditioning the particles or media such that the pH is acidic thereby inactivating said virus, and eluting said protein of interest.

13 Claims, 2 Drawing Sheets

PROTEIN PURIFICATION METHOD AND KIT

TECHNICAL FIELD

This disclosure concerns a method and a kit for combined capture/purification and virus inactivation of a feed comprising a protein of interest.

BACKGROUND

With the increasing number of protein therapeutic candidates, especially monoclonal antibodies (mAbs) entering various stages of development, biopharmaceutical companies are increasingly looking at innovative solutions to deliver this pipeline. For antibody manufacturing process development, maintaining desired quality attributes while reducing time to market, maintaining cost effectiveness, and providing manufacturing flexibility are key issues in today's competitive market. Since antibody therapies may require large doses over a long period of time, the drug substance must be produced in large quantities with cost and time efficiency to meet clinical requirements and pave the way toward commercialization. This is also the case for other recombinant therapeutic proteins including but not limited to fusion proteins, therapeutic enzymes and antibody fragments.

Generally, proteins are produced by cell culture, using cell lines, bacterial cell lines or viruses engineered to produce the protein of interest. The cell lines are fed with a complex growth medium comprising sugars, amino acids, and growth factors. For use as a human therapeutic, an amount or sample of feed (e.g., the unclarified cell culture harvest), including target molecules or target protein expressed by the cultured cells, must be treated to (i) inactivate certain of the viruses potentially present and (ii) purify and separate the desired protein from the mixture of compounds fed to the cells and from the by-products of the cells themselves. Generally, (i) and (ii) are separate steps of the desired protein purification process. In most of contemporary manufacturing processes the protein of interest is first purified and then separately treated to inactivate the viruses that are potentially contained in the feed.

Such methods are known from WO 2009/058812 A1 (D1) and Valdes et al., (2002) (D2). D1 describes a method for antibody purification based on cation exchange chromatography. The resulting purified antibody feed can subsequently be treated in order to inactivate viruses present in the feed. Similarly, D2 describes a method for protein purification and virus inactivation based on affinity purification of a target antibody on a protein A affinity chromatography column followed by a low pH treatment of the eluate to inactivate remaining viral particles. Although performing protein purification and virus inactivation in separate steps is an accepted practice, it is time-consuming and leads to an increased number of operations and time to execute them.

It is the aim of this disclosure to describe a method and a kit which overcome at least part of the above-mentioned drawbacks. Therefore, a method and a kit for combined protein capture/purification and virus inactivation are described.

SUMMARY OF THE INVENTION

In a first aspect, a method for combined virus inactivation and purification of a feed containing a protein of interest according to claim 1 is described.

More in particular, said method describes:
(a) contacting the feed with negatively charged particles or media,
(b) conditioning the particles or media such that their pH is acidic for a sufficient time after contact to inactivate one or more viruses present in said feed, and
(c) eluting said protein of interest from said separation device.

In an embodiment, a method is described for combined virus inactivation and purification of a feed containing a protein of interest, comprises the steps of:
conditioning the feed to have a conductivity of less than 15 mS/cm and a pH of at least 3,
contacting the feed with negatively charged particles or media,
conditioning the particles or media to have a pH of less than 4.5 and maintaining the pH for at least 5 min,
conditioning the particles or media such that its conductivity is at least 5 mS/cm and the pH is from 5 to 8 thereby eluting the protein of interest.

In a second aspect, a kit for combined virus inactivation and purification of a feed containing a protein of interest containing at least negatively charged particles or media, suitable solutions for conditioning the particles or media and/or the feed is described and at least one document comprising instructions to the user.

The method and the kit or this disclosure present several advantages amongst which the simplification of the protein purification process by merging two separate steps into one step and lowering the contamination risk of the final product, i.e. the protein of interest. This leads to a decrease of the production time and costs thereby lowering the cost of the final product. Furthermore, the disclosed method offers the option of continuous downstream processing of the cell culture harvest as it is devoid of a separate set-up for viral inactivation. In particular, the method provides advantages for downstream processing of the cell culture harvest where an affinity capture step is not applicable and the capture of the target molecule is performed by cation exchange chromatography. In comparison with methods which involve affinity steps in combination with low pH elution and batch viral inactivation—the disclosed method may reduce the aggregates content and even prevent aggregation of the target molecules. This is derived from performing the virus inactivation step while the molecule of interest is bound to the cation exchange separation particles or media. The disclosed method considerably increases the combined purification/inactivation yield and the quality of the purified molecules.

DETAILED DESCRIPTION OF THE INVENTION

Figure 1:
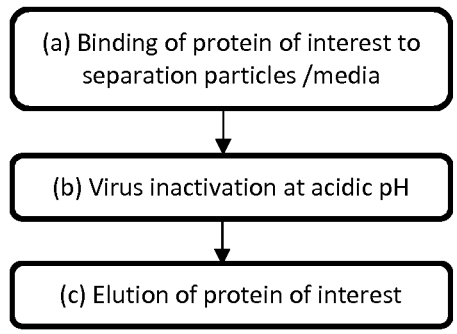
FIG. 1 shows a flow chart comprising three steps of a method for combined virus inactivation and purification of a feed containing a protein of interest according to an embodiment of the invention.

A method and a kit are disclosed for combined virus inactivation and purification of a feed comprising proteins of interest such as antibodies, antibodies derived molecules, fusion proteins, enzymes etc.

Unless otherwise defined, all terms used herein, including technical and scientific terms, have the meaning as commonly understood by one of ordinary skill in the art to which this invention belongs. By means of further guidance, term definitions are included to better appreciate the teaching of the present disclosure.

As used herein, the following terms have the following meanings:

"A", "an", and "the" as used herein refers to both the singular and plural unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation. The expression "1% w/w" refers to what can be understood as 1 g of respective component per 100 g of the formulation, the expression "1% w/v" refers to what could be understood as 1 g of respective component per 100 mL of the formulation, the expression "1% v/v" refers to what can be understood as 1 mL of respective component per 100 mL of formulation.

In a first aspect, a method for combined virus inactivation and purification of a feed containing a protein of interest comprises the steps of:

(a) contacting the feed with negatively charged particles or media, (b) conditioning the particles or media such that their pH is acidic for a sufficient time after contact to inactivate one or more viruses present in said feed, and (c) eluting said protein of interest from said particles or media.

Separation devices are devices used to separate certain impurities from sought-after target proteins. These devices include chromatography columns or cartridges with particles or media packed therein. In this disclosure, conditioning of the particles or media may either occur prior or after contacting the feed with those negatively charged separation particles or media. The method allows for the purifying of a protein of interest from a feed and the simultaneous inactivating of virus particles that may be contained in that feed. On the one hand, the separation particles or media selectively bind the protein of interest, allowing non-target molecules to be eliminated from the feed, therefore ensuring that, after elution from the separation device, a protein of interest is obtained with a high degree of purity. This high degree of purity further facilitates downstream processing of the eluate comprising the protein of interest. On the other hand, inactivation of viral particles which might be present in the feed is often essential to the utility of the protein of interest. The method enables purification of a protein of interest and simultaneous acidic inactivation of viral particles that might bind to the separation particles or media in addition to the protein of interest. This leads to elution of the protein of interest in a purified state, with a decreased content of impurities and without certain active viral particles that are sensitive to acidic viral inactivation which might compromise further use of the protein of interest. Performing these two processing steps as a single step therefore allows to further streamline the purification process, rendering it more efficient and less time consuming.

The protein of interest may be an antibody, an antibody fragment, an antibody derivative or a fusion protein. The protein of interest can also be any other recombinant protein such as an enzyme, a peptide or a polypeptide or other biomolecules expressed by the cells.

In an embodiment, prior to step (a) the pH of said feed is adjusted such that it is below the isoelectric point (pI) of said protein of interest. In another or further embodiment, the feed is conditioned towards a preferred conductivity. By preference, said conductivity is at most 25 mS/cm.

It is to be understood that conditioning of the feed's conductivity and/or the pH might be achieved by any method known to the person skilled in the art including dilution, buffer exchange, titration or any combination thereof. Conditioning of the particles or media conductivity and pH is achieved by flowing through said particles or media a sufficient volume of a solution having the target conductivity and/or pH. A conditioning aiming at decreasing the conductivity of a feed could be achieved by diluting the feed with ultrapure water or with low-salt buffering solution such as 20 mM sodium acetate pH 5.3. A conditioning that aims at increasing the conductivity of a feed might be achieved by titration of the feed with 5 M sodium chloride solution until reaching the desired conductivity. The pH of a solution might be lowered using a 0.2M to 1.0M hydrochloric acid solution or 1M acetic acid. The pH of a solution might be increased using a 0.2M to 1.0M sodium hydroxide or with 2M TRIS base pH 9.50.

In an embodiment, the feed is conditioned prior to step (a) such that the conductivity of said feed is at least 0.1 mS/cm, at least 2 mS/cm, at least 3 mS/cm, at least 4 mS/cm, at least 5 mS/cm or any intermediate value. The conductivity of the feed is at most 25 mS/cm, at most 13 mS/cm, at most 12 mS/cm, at most 10 mS/cm, at most 7 mS/cm, at most 6 mS/cm, 5.5 mS/cm or any intermediate value. The feed comprising a protein of interest is also conditioned prior to step (a) such that the pH of the feed is below the isoelectric point (pI) of said protein of interest. The pH of the feed is at least 3, at least 4, at least 4.5, at least 5 and at most 9, at most 8, at most 7, at most 6 or any intermediate value. The conditioning of the feed prior to step (a) leads to a net positive surface charge of the protein or molecule of interest and/or to a conductivity that favors the binding of said molecule to the particles or media, in particular a cation exchange particles or media. The conditioning ensures proper capture of the protein of interest and increases the dynamic binding capacity of the particles or media.

In a further embodiment, the method comprises the steps of:
- conditioning the feed such that its conductivity is at most 15 mS/cm and its pH is at least 3,
- contacting the feed with negatively charged separation particles or media, thereby binding the protein of interest to the separation particles or media,
- conditioning the separation particles or media such that its pH is acidic [at most 4.5] and maintain said pH for at least 1 min, or at least 5 min, thereby inactivating viruses,
- conditioning the separation particles or media such that its conductivity is at least 5 mS/cm and its pH is of from 5 to 8 thereby eluting the protein of interest.

The inventors have found that the above mentioned conditions were especially favorable for good binding of the protein of interest to the separation particles or media on the one hand and for the simultaneous inactivation of the virus on the other hand.

For the purpose of the current disclosure, a feed is any material or solution comprising the desired protein. Preferably, the feed is at least one cell culture harvest which is obtainable by growing cells in at least one cell culture vessel such as a bioreactor until reaching a predetermined point of the process. A feed is a sample or an amount of a cell culture harvest. A feed or cell culture harvest is optionally clarified prior to being treated per the disclosed method.

In an alternate embodiment, the method further comprises the step of clarifying the feed prior to step (a). Wherein the feed is a cell culture harvest, said clarification might be performed when the cell culture is inside and/or outside the cell culture vessel or bioreactor. The clarification can be achieved by any method known to the person skilled in the art.

In the instance when the feed is a cell culture harvest grown in a suspension environment, the clarification of the unclarified feed comprising a cell culture starts with determining the wet cell weight (WCW) of the cell culture grown in suspension. The WCW can be determined according to any method known to the person skilled in the art. The WCW may be determined as follows: cell culture feeds are withdrawn from the bioreactor after reaching the predetermined cell density. In an embodiment, at least 3 feeds of 15 to 50 ml each are collected. The feeds are centrifuged at 4000 to 5000 g for 5 to 10 minutes to sediment cells. The obtained supernatant is discarded and WCW is calculated based on the difference between the weight of empty centrifugal tubes and the weight of the centrifugal tubes containing settled-down cells. The average of the three measurements is calculated and recorded as WCW in gram per liter.

The clarification of the unclarified feed comprising a cell culture comprises the addition to said culture of a fatty acid having 7 to 10 carbon atoms, allantoin, at least one electropositive compound, diatomaceous earth (DE) or any combination thereof. These compounds might be in liquid or solid form and might be introduced as a mixture or separate from each other.

0.3% to 0.6% v/v fatty acid, 0.5% to 3% w/v allantoin and 0.01% to 1% w/v at least one electropositive compound may be used for the clarification of the feed. In another or further embodiment, said 0.4% to 0.5% w/v fatty acid, 1% to 2% w/v allantoin and 0.05% to 0.1% w/v at least one electropositive compound are used for the clarification of the feed.

The molecular weight of the chitosan may be of from 30 kDa to 1000 kDa. Said chitosan might have any degree of acetylation.

In an embodiment, the electropositive compound is any electropositive charged particle such as electropositive polysaccharide, electropositive polymer, chitosan, chitosan derivatives, synthetic polymers such as polydiallyl dimethylammonium chloride (pDADMAC or polyDDA), benzylated poly(allylamine) and polyethylenimine, commercially available particles like TREN (BioWorks, WorkBeads TREN, high) or cationic surfactants like hexadecyltrimethylammonium bromide (also known as CTAB).

In another embodiment, the general structural formula of the fatty acid is $CH_3(CH_2)_nCOOH$, wherein n is an integer from 4 to 12 inclusive, or from 5 to 8 inclusive. The fatty acid may be enanthic acid (heptanoic acid), caprylic acid (octanoic acid), pelargonic (nonanoic acid), capric acid (decanoic acid), nonenoic acid or any combination thereof. The fatty acid may be added in the form of a salt, such as a sodium salt, for example sodium caprylate. The fatty portion of the fatty acid may consist of a linear "straight" chain of carbon atoms. In some embodiments, the fatty portion of the fatty acid may consist of a branched chain, such as 2-ethylhexanoic acid, which contains a 2-carbon chain at the number 2 position of the primary 6-carbon chain, producing a total of 8 carbon atoms. The fatty acid may include a double bond at any position in the carbon chain. The fatty acid chain may contain 6 or 7 or 8 or 9 carbon atoms.

In yet another embodiment, the fatty acid, allantoin and the at least one electropositive compound are added to the cell culture inside the bioreactor and are left in said bioreactor for 5 to 360 minutes, for 15 to 240 minutes, for 60 to 120 minutes, for 30 to 60 minutes, or for an intermediate interval. The cell culture is agitated at 60 to 120 rpm at a room temperature or above room temperature up to of about 37° C.

In still yet another embodiment, the DE is added to the cell culture after addition of the fatty acid, allantoin and the electropositive compound and agitation under the conditions mentioned above. The DE amount added is of from 20 to 60%, from 25 to 45%, or from 30 to 48%, from 35 to 45%, or about 40% of the WCE of the cell culture. DE can be of various grades that are commercially available on the market. For example, for CHO cell cultures, Celpure 300® grade or Celpure 1000® grade can be used, depending on the bioreactor.

In an embodiment, DE may be added after 45 min counting from the addition of the fatty acid, allantoin and the electropositive compound. After addition of DE, agitation is maintained for 5 to 60 min, for 8 to 40 min, for 10 to 30 min, for 15 to 20 min. Agitation is maintained at 60 to 180 rpm. The cell culture is then filtered using at least one filtration means which is impermeable to DE. Said filtration means is at least partially permeable to at least some components of the unclarified cell culture such including small host cell impurities, and is fully permeable to the proteins or molecules of interest.

Upon the introduction of the cell culture into the filtration means, the DE cumulates on one side of the filtration means and gradually builds-up into a DE structure comprising a plurality of channels. The size or the diameter of the channels is defined by the particle size of the DE added to the first solution. The DE particle size may be chosen according to the size of the biomolecule of interest and/or the properties of the cell culture and/or the properties of the cells used to express the molecule of interest (this includes the type of cells (e.g. CHO cells) and the cell density of the harvest to be clarified). The formed DE structure serves as a filtration tool. The large material such as cells, cell debris, and non-target molecules are retained by the DE structure, whereas the target biomolecules, having a small size, flow through the channels of the DE structure. A clarified cell culture comprising the protein of interest is thereby obtained. Optionally, a depth filter is positioned downstream the DE structure and the filtration means. The depth filter is chosen such that the protein of interest passes though it while retaining other eventual contaminants or impurities. This further reduces the presence of contaminant in the clarified cell culture. Clarification of the feed or the cell culture using DE improves the filterability of the treated/flocculated cultured cells by removing at least partially cells impurities and other non-target molecules from the feed.

The negatively charged particles or media may be a cation exchange resin. Said particles or media can be any cation-exchange chromatography media or particles. Said media or particles may be packed in a column or used as a membrane commercially available on the market. Furthermore, said chromatography media, column or membrane can be of multimodal nature with cation exchange properties, e.g. salt tolerant cation exchangers, cation exchangers with hydrophobic moieties etc. Said column is prepared for use preferably according to vendor's manual. After preparation, said column may be conditioned to have parameters, i.e. pH and conductivity, equal, similar or close to the parameters of the feed containing the target molecule. The chromatography media can be a so-called "strong" cation exchanger as well as so-called "weak" cation exchanger. The separation particles or media can also be a separation membrane comprising functional groups or so-called membrane adsorber. By preference, said particles or media are packed in a column or cartridge.

The clarified and conditioned feed is afterwards brought in contact with the particles or media. This can be achieved by introducing the feed into a chromatography column packed with particles or media or bringing it in contact with the particles or media. The contact between the clarified feed and the particles or media can be performed manually or automatically using suitable tubing and/or pumps and/or a chromatography instrument.

As non-target molecules might bind to the particles or media, at least one washing step is optionally performed. The washing step can be performed before and/or after the viral inactivation step of the method. In a further embodiment, the separation particles or media are washed by:
  introducing to the particles or media the solution used for equilibrating them, and/or
  conditioning the particles or media such that its conductivity is below the protein elution conductivity, from 7 to 15 mS/cm and/or conditioning its pH to a pH that is below the protein elution pH, from 3 to 8. This washing removes non-target molecules from the separation particles or media while maintaining the protein of interest bound to said separation particles or media. This increases the purity of the protein of interest which will be eluted at a later stage.

In an embodiment, the particles or media during the viral inactivation are conditioned to have a low pH thereby inactivating the viruses present in the feed. Additionally, lowering the pH of the separation particles or media results in an increased net positive charge of the proteins of interest due to gain of protons ($H^+$) from the acidic environment. This ensures viral clearance of the fraction that will be eluted and chromatography capture/purification in contrast to known approaches wherein the two steps are performed separately. The pH of the separation particles/media is preferably lowered using a suitable buffering solution. Said pH is lowered such that it is at least 2, at least 2.5, at least 3, at least 3.4, at least 3.6 or any intermediate value. Said pH is at most 4.5, at most 4.3, at most 4, at most 3.9, at most 3.8, at most 3.7 or any intermediate value. Lowering the pH of the separation particles or media leads to the inactivation of the viruses present in the feed. The low pH of the separation particles or media is maintained for at least 1 min, at least 15 min, at least 25 min, at least 35 min, at least 45 min, at least 60 min or any intermediate value. Said low pH is maintained for at most 4 hours, at most 3 hours, at most 2 hours, at most 1 hour or any intermediate value. The low pH of the separation particles or media can be maintained by completely stopping or maintaining a low flowrate through the separation particles or media. Flowrate can vary depending on the process and may be from 0 to 600 cm/h. The flowrate may be of at most 600 cm/h, at most 500 cm/h, at most 400 cm/h, at most 300 cm/h or any intermediate value. Said flowrate is of at least 50 cm/h, at least 100 cm/h, at least 150 cm/h, at least 200 cm/h or any intermediate value. Optionally, at least one agent facilitating viral clearance is added to the buffering solution used during the viral inactivation step. The concentration of the viral clearance-facilitating agent is of from 0.01 to 10% v/v, from 1 to 8% v/v, from 3 to 7% v/v, about 5% v/v and preferred viral inactivation agent is isopropyl alcohol. Additionally, the viral inactivation washing solution can also contain triton X-100 and tri-n-butyl phosphate or any combination thereof to facilitate viral clearance.

In an embodiment, after virus inactivation, the conductivity of the separation particles/media is maintained constant, i.e. is at most 7 mS/cm and at least 0.1 mS/cm while its pH is adjusted to a pH of 3 to 9, from 6 to 8, from 5 to 8. The pH adjustment serves to (i) prepare for the elution of the protein of interest while maintaining said protein bound to the separation particles or media. Indeed, elution in neutral pH conditions considerably lowers the aggregation risk of the protein of interest which tend to aggregate under acidic conditions and (ii) achieve higher purity of the protein as impurities remaining in the separation particles or media elute due to the pH shift while the protein of interest remains bound to the separation particles or media. This increases the purity of the protein of interest which will be eluted.

Afterwards, the separation particles or media are conditioned such that their conductivity is at least 1 mS/cm, at least 5 mS/cm, at least 7 mS/cm, at least 7.5 mS/cm, at least 8 mS/cm, at least 9 mS/cm and at least 10 mS/cm. Said conductivity is at most 50 mS/cm, at most 20 mS/cm, at most 14 mS/cm, at most 13 mS/cm, at most 12 mS/cm and at most 11 mS/cm. This leads to the elution of the protein of interest in a purified state and with no or decreased content of impurities and/or aggregates.

In a second aspect, a kit for combined virus inactivation and purification of a feed containing a protein of interest contains at least one negatively charged separation particles or media, which may be packed in a column, suitable solutions for conditioning the separation particles or media and/or the feed as described above and at least one document comprising instructions to the user.

Figure 2:
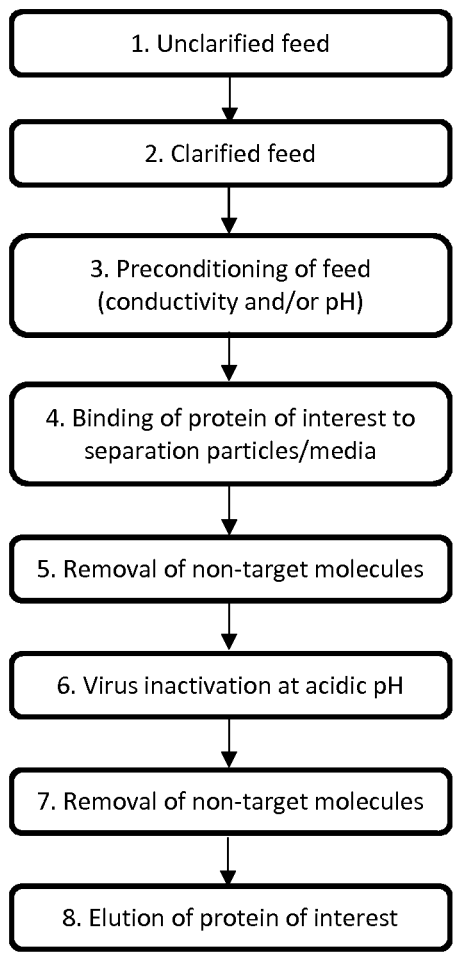
FIG. 2 shows a flow chart of a method for combined virus inactivation and purification of a feed containing a protein of interest according to an embodiment of the invention.

FIGS. 1 and 2 show flow charts of methods according to embodiments of the disclosure. The flowchart in FIG. 1 shows the general outline of the concept. In first step a, the protein of interest present in a feed binds to separation particles or media which are negatively charged. In step b, viruses present in the feed are inactivated by conditioning the particles or media such that an acidic pH is reached, which also enables binding of the protein to the separation particles or media. Finally, the protein of interest is eluted in a step c).

FIG. 2 illustrates the steps of possible methodology. In a first step 1, an unclarified feed is provided which in step 2 will be optionally clarified by removal of particulate matter. In an optional step 3, the feed is preconditioned towards a preferred conductivity and/or pH. The feed is then brought into contact with the separation particles/media which are normally packed in a column or cartridge. In a subsequent step (step 6), the separation particles/media are conditioned towards an acidic pH. This pH will allow binding of the protein of interest but also inactivate any viruses present in the feed. Note that either of the steps 2 and 6 can be accomplished before the other depending on the embodiment. Optionally, in a step 5 and 7, washes may be performed to remove non-target molecules. In a final step 8, the protein will be eluted from the particles or media, resulting in purified protein of interest.

EXAMPLES

Example 1: IgG1 Monoclonal Antibody Purification and Rodent Virus Inactivation from a CHO Cell Culture Feed IgG1 monoclonal antibody was purified from a CHO cell culture feed based on a method according to a possible embodiment. FIG. 2 illustrates the sequence of steps during the purification and virus inactivation of the IgG1 monoclonal antibody. CHO cell culture unclarified harvest (FIG. 2—Step 1) was treated with caprylic acid (0.45% v/v), allantoin (1% w/v), high molecular weight chitosan (0.08% w/v) and diatomaceous earth of Celpure 300© grade (38% w/w of wet cells weight) and clarified (FIG. 2—Step 2) by body feed filtration with diatomaceous earth at pH of 5.30. The cell culture expressed IgG1 monoclonal antibody with theoretical isoelectric point of 8.61.

After the above clarification, the harvest was further clarified with Sartoclear DL20 depth filter. The clarified harvest was diluted to a conductivity of 5 mS/cm with ultrapure water (FIG. 2—Step 3). The pH of the clarified harvest was adjusted to 5.3 with 1M acetic acid (FIG. 2—Step 3). A strong cation exchange media Toyopearl GigaCap S-650M, prepacked in a 5 ml column volume (CV) chromatography column, with bed dimensions of 8 mm×100 mm, was used as a capture/virus inactivation means, and the following procedure was applied:

the chromatography column was sanitized with 0.5N sodium hydroxide for 60 minutes with a flowrate of 100 cm/h and then neutralized with 50 mM HEPES pH 7.0, 5 CV at 600 cm/h;

the cation exchange media was conditioned with 50 mM sodium acetate, 1M sodium chloride pH 5.30 for 10 CV with a linear flowrate of 600 cm/h;

the cation exchange media was equilibrated with 50 mM sodium acetate, sodium chloride with conductivity of 5.0 mS/cm, pH 5.3 for 10 CV at a flowrate of 600 cm/h;

the clarified harvest containing the protein of interest was loaded to the column at 600 cm/h (FIG. 2—Step 4);

the cation exchange media was washed (wash 1, FIG. 2—Step 5) with an equilibration buffer: 50 mM sodium acetate, sodium chloride having a conductivity of 5.0 mS/cm for 5 CV at a flowrate of 600 cm/h;

viral inactivation was performed (wash 2, FIG. 2—Step 6) by passing 50 mM sodium acetate, pH 3.70 solution through the cation exchange media at 100 cm/h for 60 minutes;

the cation exchange media was washed (wash 3, FIG. 2—Step 7) with the equilibration buffer: 50 mM sodium acetate, sodium chloride having a conductivity of 5.0 mS/cm for 5 CV at a flowrate of 600 cm/h;

the cation exchange media was washed (wash 4) with 50 mM sodium acetate, sodium chloride, conductivity of 11 mS/cm, pH 5.30 for 7 CV at a flowrate of 600 cm/h;

the protein of interest was eluted (FIG. 2—Step 8) with 50 mM sodium acetate, sodium chloride, conductivity of 14.5 mS/cm, pH 5.30 at a flowrate of 150 cm/h;

the cation exchange media was stripped with 50 mM sodium acetate, 1M NaCl pH 5.30 for 5 CV at a flowrate of 600 cm/h;

the cation exchange media was sanitized with 0.5N NaOH for 60 minutes with a flowrate of 100 cm/h and stored in 50 mM HEPES, 20% v/v ethanol pH 7.0.

Figure 3:
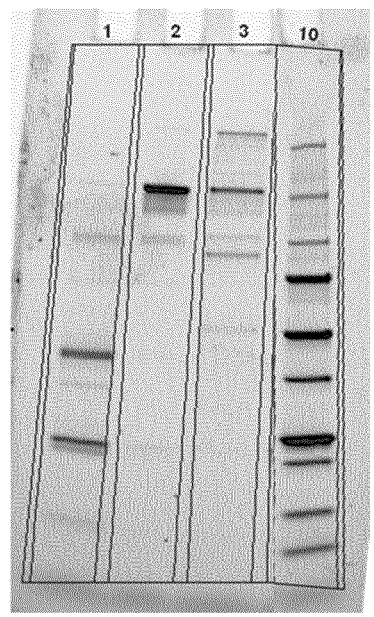
FIG. 3 shows an SDS PAGE electrophoregram of a wash fraction and a target protein fraction both obtained according to the method of the invention.

The protein of interest was eluted and collected in different fractions which were analyzed. The target protein concentration in the flow-through fraction was monitored using Fc-ELISA assay and the results were negative in each collected fraction as well as in the flow-through pool. The wash fractions and elution fractions were analyzed by SDS-PAGE (FIG. 3) which confirmed that the wash fractions (lane 1 in FIG. 3) contain mostly LMW impurities and very minor percentage of the protein of interest. The elution fraction (lane 2, FIG. 3) contained the target antibody. Lane 3 of FIG. 3 shows a strip and lane 10 of FIG. 3 shows a molecular weight marker. The content of the host cell proteins in the elution fraction has been monitored using commercially available HCP ELISA kit from Cygnus Technologies, and concentration of HCPs in the elution fraction was estimated to be about 500 ppm.

Example 2: IgG1 Monoclonal Antibody Purification and Virus Inactivation from a CHO Cell Culture Feed IgG1 monoclonal antibody was purified from a CHO cell culture feed based on a method according to an embodiment of the invention. FIG. 2 illustrates the sequence of steps during the purification and virus inactivation of the IgG1 monoclonal antibody. CHO cell culture unclarified harvest (FIG. 2—Step 1) was treated with caprylic acid (0.45% v/v), allantoin (1% w/v), high molecular weight chitosan (0.08% w/v) and diatomaceous earth of Celpure 300 grade (38% w/w of wet cells weight) and clarified (FIG. 2—Step 2) by body feed filtration with diatomaceous earth at pH of 5.30. The cell culture expressed IgG1 monoclonal antibody with theoretical isoelectric point of 8.61.

After the above clarification, the harvest was further clarified with Millipore B1HC depth filter. The clarified feed was diluted to conductivity of 5 mS/cm with ultrapure water (FIG. 2—Step 3). The pH of the clarified harvest was adjusted to 5.3 with 1M acetic acid (FIG. 2—Step 3). A cation exchange media Toyopearl GigaCap S-650M, prepacked in a 5 ml column volume (CV) chromatography column, with bed dimensions of 8 mm×100 mm, was used as a capture/virus inactivation means, and the following procedure was applied:

the chromatography column was sanitized with 0.5N sodium hydroxide for 60 minutes with a flowrate of 100 cm/h and then neutralized with 50 mM HEPES pH 7.0, 5 CV at 600 cm/h;

the cation exchange media was conditioned with 30 mM sodium acetate, 1M NaCl pH 5.30 for 10 CV at a flowrate of 600 cm/h;

the cation exchange media was equilibrated with 30 mM sodium acetate, sodium chloride having a conductivity of 5.0 mS/cm, pH 5.30 for 10 CV at a flowrate of 600 cm/h;

the clarified harvest containing the protein of interest was loaded to the column at 600 cm/h (FIG. 2—Step 4);

the cation exchange media was washed (wash 1, FIG. 2—Step 5) with equilibration buffer 30 mM sodium acetate, sodium chloride having a conductivity of 5.0 mS/cm for 5 CV at a flowrate of 600 cm/h;

the cation exchange media was washed (wash 2, FIG. 2—Step 5) with 30 mM sodium acetate, sodium chloride with conductivity of 11 mS/cm, pH 5.3 for 7 CV with linear flowrate of 600 cm/h;

viral inactivation was performed (wash 3, FIG. 2—Step 6) by passing 30 mM sodium acetate, sodium chloride with conductivity 5 mS/cm, pH 3.7 for 45 minutes with linear flowrate of 100 cm/h;

the cation exchange media was washed (wash 4, FIG. 2—Step 7) with 30 mM HEPES, sodium chloride with conductivity of 5 mS/cm, pH 7.2 for 6 CV with a flowrate of 600 cm/h;

the protein of interest was eluted (FIG. 2—Step 8) with 20 mM HEPES, sodium chloride, conductivity of 12 mS/cm, within 4 CV with a linear flowrate of 150 cm/h;

the cation exchange media was stripped with 20 mM HEPES, 1M sodium chloride, pH 7.2 for 5 CV at linear flowrate of 600 cm/h;

the cation exchange media was sanitized with 0.5N sodium hydroxide for 60 minutes with a flowrate of 100 cm/h and stored in 50 mM HEPES, 20% v/v ethanol pH 7.0.

Figure 4:
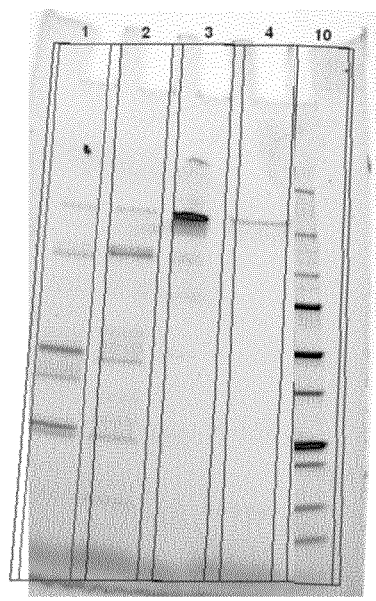
FIG. 4 shows an SDS PAGE electrophoregram of wash fractions and a target protein fraction obtained according to the method of the invention.

The protein of interest was eluted and collected in different fractions which were analyzed. The target protein, i.e. the antibody, concentration in the flow-through fraction was monitored using Fc-ELISA assay and the results were negative in each collected fraction as well as in the flow-through pool. The wash fractions and elution fractions were analyzed by SDS-PAGE (FIG. 4) which confirmed that the wash fractions (lanes 1 and 2 in FIG. 4) contain mostly LMW impurities and very minor percentage of the protein of interest. The elution fraction (lane 3, FIG. 4) contained the target antibody. Lane 4 of FIG. 4 shows a strip and lane 10 of FIG. 4 shows a molecular weight marker. The content of the host cell proteins in the elution fraction has been monitored using commercially available HCP ELISA kit from Cygnus, and concentration of HCPs in the elution fraction was estimated to be about 500 ppm.

It is supposed that the present invention is not restricted to any form of realization described previously and that some modifications can be added to the presented example without reappraisal of the appended claims.

The invention claimed is:

1. A method for combined virus inactivation and purification of a feed containing a protein of interest comprising the steps of:
   (a) contacting the feed with negatively charged particles or media,
   (b) conditioning the particles or media such that their pH is at least 2.5 and at most 4.3 for at least one minute after the particles or media contact the feed to inactivate one or more viruses present in said feed, and
   (c) eluting said protein of interest from said particles or media.

2. The method according to claim 1 wherein, prior to step (a), the pH of said feed is adjusted such that it is below the isoelectric point (pI) of said protein of interest.

3. The method according to claim 1 wherein prior to step (a) the feed is conditioned such that the conductivity of said feed is at most 25 mS/cm.

4. The method according to claim 1, wherein elution of said protein occurs at a pH of 3 to 9.

5. The method according to claim 1, wherein elution of said protein occurs at a conductivity of at least 0.1 mS/cm.

6. The method according to claim 1,
   wherein the conditioning step includes conditioning the feed such that its conductivity is at least 5 mS/cm and at most 15 mS/cm and its pH is at least 3.

7. The method according to claim 1, wherein the feed is conditioned prior to contacting said feed with said particles or media such that the conductivity is at least 0.1 mS/cm and at most 25 mS/cm and/or such that its pH is at least 3 and at most 9.

8. The method according to claim 1, wherein during step (b), the pH of at least 2.5 and at most 4.3 of the particles or media is maintained for at least 1 min and at most 4 hours after the particles or media contacts the feed.

9. The method according to claim 1, wherein the particles or media during elution are conditioned such that their conductivity is at least 1 mS/cm and at most 50 mS/cm.

10. The method according to claim 1, wherein the feed is a clarified feed.

11. The method according to claim 10 wherein the clarification of said feed comprises adding to the feed at least one fatty acid having 7 to 10 carbon atoms and/or allantoin; at least one electropositive compound selected from the group comprising electropositive polysaccharide, electropositive polymer, chitosan, a chitosan derivative, a synthetic polymer, polydiallyl dimethylammonium chloride (pDADMAC), a cationic surfactant; and diatomaceous earth or any combination thereof.

12. The method according to claim 1 further comprising:
   removing non-target molecules from said particles or media, and/or
   conditioning the pH of the particles or media by dilution, buffer exchange, titration or any combination thereof.

13. The method of claim 1 wherein the contacting step comprises introducing the feed into a separation device having negatively charged particles and media.

* * * * *